(12) United States Patent
Wagner et al.

(10) Patent No.: US 6,837,399 B1
(45) Date of Patent: Jan. 4, 2005

(54) DYNAMIC MIXER

(75) Inventors: Ingo Wagner, Steinebach (DE); Hermann Nirschl, Seefeld (DE)

(73) Assignee: 3M ESPE AG, Seefeld (DE)

( * ) Notice: Subject to any disclaimer, the term of this patent is extended or adjusted under 35 U.S.C. 154(b) by 452 days.

(21) Appl. No.: 10/089,519

(22) PCT Filed: Sep. 27, 2000

(86) PCT No.: PCT/EP00/09447

§ 371 (c)(1),
(2), (4) Date: Mar. 29, 2002

(87) PCT Pub. No.: WO01/24919

PCT Pub. Date: Apr. 12, 2001

(30) Foreign Application Priority Data

Oct. 1, 1999 (DE) .......................................... 199 47 331

(51) Int. Cl.[7] ................................................. B67D 5/52
(52) U.S. Cl. ......................... 222/145.6; 222/1; 222/325; 366/172.1; 366/175.1; 366/180.1; 366/181.5; 366/230; 433/89
(58) Field of Search .......................... 366/176.1, 176.3, 366/180.1, 181.5, 181.3, 225, 230, 336–340, 155.1, 158.5, 172.1, 173.1, 174.1, 175.1, 175.2; 222/1, 135, 145.6, 325, 326, 386; 433/89

(56) References Cited

U.S. PATENT DOCUMENTS

| | | | |
|---|---|---|---|
| 3,831,850 A | 8/1974 | Hunter | ........................ 239/144 |
| 5,249,862 A | * 10/1993 | Herold et al. | ................ 366/312 |
| 5,487,606 A | 1/1996 | Keller | ......................... 366/339 |
| 6,244,740 B1 | 6/2001 | Wagner et al. | ............ 366/181.5 |
| 6,394,643 B1 | * 5/2002 | Bublewitz et al. | ........ 366/172.1 |
| 6,523,992 B1 | * 2/2003 | Bublewitz et al. | ........ 366/172.1 |

FOREIGN PATENT DOCUMENTS

| | | |
|---|---|---|
| DE | 14 54 798 | 3/1969 |
| DE | 32 37 353 | 4/1984 |
| DE | 35 22 087 | 1/1987 |
| DE | 297 05 741 | 8/1998 |
| DE | 197 37 007 | 12/1998 |
| EP | 0 492 412 | 7/1992 |
| EP | 0 993 863 | 9/1999 |

* cited by examiner

Primary Examiner—Gene Mancene
Assistant Examiner—Patrick Buechner
(74) Attorney, Agent, or Firm—Crowell & Moring LLP

(57) ABSTRACT

The invention relates to a dynamic mixer, comprising a housing (10) and an inner body (11) which can be rotated about a common axis in relation to each other and which form a mixing chamber (12); a back shut-off element (20) which delimits the mixing chamber (12) and which has inlet openings (21) for guiding in the components to be mixed, a front outlet (24) for delivering the mixture and a drive element (17) which is located on the rotatable part of the mixer. The inner body (11) is connected to the shut-off element (20) and forms the stator of the mixer, while the housing (10) is provided with the drive (17) and forms the rotor of the mixer.

31 Claims, 3 Drawing Sheets

Figure 1:
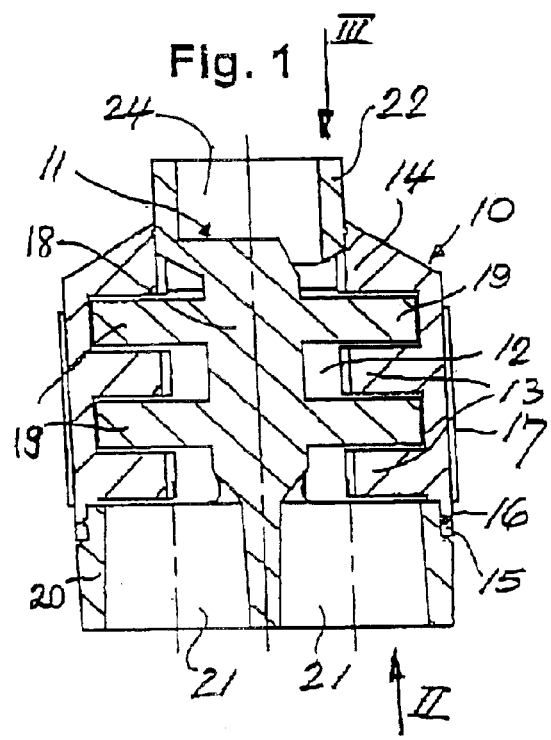

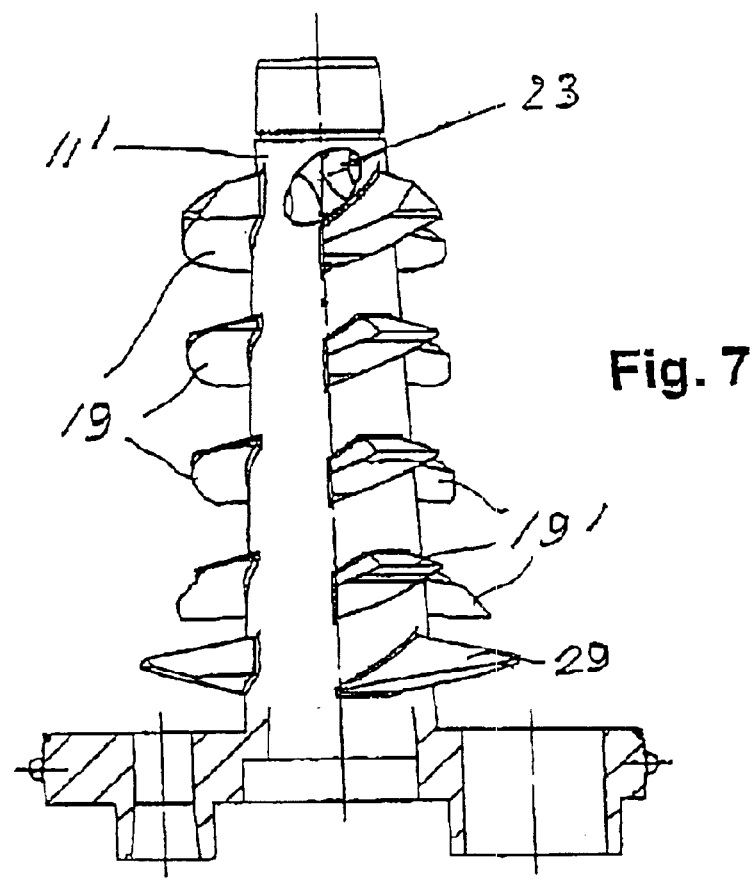
Fig. 7
Fig. 8
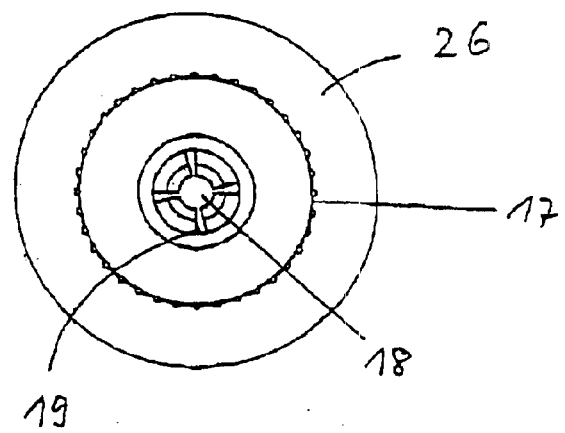

DYNAMIC MIXER

The invention relates to a dynamic mixer which is used in particular in the dental sector for mixing, inter alia, highly viscous pastes.

In order to mix highly viscous pastes containing two or more components, in particular dental impression compounds, use is made of static and dynamic mixers. Examples of dynamic mixers are found in EP-A-0 492 412 and DE-U1-297 05 741.

The known dynamic mixers have, at their rear end (inlet side), a central hexagonal opening for coupling a drive shaft for the rotating inner body of the mixer and also inlet connectors for feeding the components which are to be mixed. When a new mixer is fitted in place, it is first necessary for three connections to be aligned at the same time with the corresponding counterparts of the discharging apparatus, this resulting in comparatively complicated handling.

The central connection for coupling the mixer shaft further results in the inlet connectors for the components being comparatively remote from the mixer axis. This means that comparatively small cross sections are left over for the inlet connectors or the component strands in the inlet region have to be deflected inward to a comparatively pronounced extent if it is not acceptable to have an unnecessarily large mixer. In both cases, there is a comparatively high flow resistance for the components, which results in high advancement and mixing forces.

In the known mixers, it is only the rotating inner mixer body which is provided with mixing blades, while the inner wall of the mixer housing is smooth. In order to achieve sufficiently homogenous mixing with such mixers, a corresponding axial length is necessary. This, in turn, results in an undesirably high residual quantity remaining in the mixer.

It is an object of the invention to provide a dynamic mixer in which the problems arising in the prior art are avoided at least in part. A more specific object of the invention may be seen in specifying a dynamic mixer, in particular for dental compounds, which allows the components to be mixed thoroughly by relatively straightforward means.

This object is achieved by a mixer and a mixing arrangement comprising the latter, as is described in the claims.

The terms "comprise" and "contain", within the context of the invention, introduce an open-ended list of features here.

The term dynamic mixer is to be understood as meaning mixers in which, in contrast to static mixers, at least one constituent part is mounted rotatably.

The term mixing chamber describes the region of the mixer where the actual mixing of the substances entering through the inlet openings predominantly takes place. The mixing-chamber filling volume which is required for mixing purposes is basically of any desired magnitude and may be selected in dependence on the purpose for which the mixer is used and the properties of the substances which are to be mixed. The filling volume conventionally lies in the range of from 0.1 to 10 ml, preferably in the range of from 0.5 to 3 ml.

Inlet openings are intended to be understood as meaning the openings in the rear region of the mixer which the substances which are to be mixed have to pass in order to reach the mixing chamber. The inlet openings are part of the termination element or form the latter in its entirety.

The openings are basically of any desired shape. Oval openings and/or kidney-shaped or sickle-shaped openings, in particular openings with rounded edges and corners, are advantageous.

This configuration makes it possible to utilize virtually the entire surface area of a dynamic mixer which is available for the inlet openings. A cutout for a mixer shaft which can be coupled centrally is not necessary.

The apparatus according to the invention preferably has at least two, but possibly also three or four openings.

The openings are usually arranged symmetrically to one another.

The outlet is intended to mean the region of the mixer through which the substances leave the actual mixing space.

The mixer may have one or more outlet openings, preferably two, three or four outlet openings. The outlet openings may be arranged in a manner of a strand divider, but it is also possible for them to open out into a further cavity, via which the mixed substances are eventually discharged. The outlet opening or openings may thus also be located within the mixer.

The term drive region covers, in particular, the region of the mixer via which the rotor can be made to rotate by the action of external forces. The drive region is expediently configured such that force transmission can take place with the lowest possible level of losses.

Depending on the type of force transmission, which may be non-positively and/or positively locking, the drive region has carry-along elements, grooves, gearwheels and/or a roughened surface. It may also be favorable to apply a friction-enhancing additional element, for example in the form of a rubber-like ring, to the surface of the drive region.

The drive region is located eccentrically in relation to the common axis, preferably on the outside of the housing.

The term stator is intended to be understood, in contrast to the term rotor, as meaning the element or elements of the mixer which is/are not desired to be made to rotate by the action of external forces during the mixing operation.

The mixer according to the invention has, inter alia, the following advantages:

Since the inner body of the mixer forms the stator and the housing forms the rotor, it is possible for the inlets for the components to be arranged in close proximity to the mixer axis, with the result that, despite the small overall cross section of the mixer, comparatively large cross-sectional surface areas are available to the inlet openings. On account of the relatively large inlet cross sections, the arrangement manages with relatively small advancement forces.

During operation of the mixer, lower throughflow forces occur than in the mixers known from the prior art since, as a result of the drive of the mixer, via the housing, more rectilinear guidance of the substance streams is possible. In addition, this makes possible a relatively compact construction of the mixer.

If the inlet openings are all of the same shape and size, the task of fitting the mixer on outlet openings of cartridges, in which the substances which are to be mixed may be located, is additionally facilitated since there is no need to bother with orienting the inlet openings relative to the outlet openings of the cartridge.

Furthermore, there is no need for additional introduction of a mixer shaft, when the mixer is positioned on the discharging openings of the cartridge, in the absence of the connection for a central mixer shaft.

The drive element is preferably arranged outside the axis about which the rotor is rotated. An arrangement outside the mixer axis for engagement with the drive of the respective discharging apparatus is advantageous because the comparatively large diameter results in a corresponding long lever arm, by means of which the torque required for driving the rotor can be transmitted more easily.

At the same time, the task of fitting the mixer in place on the discharging apparatus is facilitated since, instead of the six angle positions provided for in the case of the hexagonal opening according to the prior art, a much larger number of appropriate positions may be provided on the relatively large external diameter provided according to the invention if use is made of one or more gearwheels.

A configuration of the mixer in which the drive element is located on the outer circumference of the housing allows a compact construction and straightforward coupling of the drive.

A non-positively locking drive can improve the handling of the mixer such that alignment problems when the mixer is fitted in place are largely avoided. In addition, simplified cleaning of the drive is possible.

The presence of mixer blades both on the rotor and on the stator allows relatively intensive mixing on account of the shearing of the components which occurs over the entire flow cross section of the mixing chamber, with the result that it is possible for the overall size of the mixer, in particular the axial length thereof, to be reduced to a considerable extent in comparison with conventional mixers, without the mixing result being affected to any significant extent.

The volume of the mixing chamber can be reduced on the one hand, by the overall length of the mixer being reduced in comparison with the prior art and/or, on the other hand, by additional mixing blades being integrally formed in the mixing chamber.

The present invention thus allows a considerable reduction in the quantity of mixed substance discarded, this being determined decisively by the volume of the mixing chamber.

The mixer blades are usually arranged symmetrically on an annular place on the outside of the inner body and the inside of the housing. Preferably, two, three or four mixer blades are located in each annular plane.

There is basically any desired number of annular planes, depending on the dimension of the mixing chamber. Furthermore, the number which is to be selected may be selected in dependence on the purpose for which the mixer is to be used and the properties of the substances which are to be mixed. In the dental sector, a number of annular planes in the range of from two to eight, preferably of from two to four, has proven successful for mixing highly viscous substances. It is also favorable if the number of annular planes on the inside of the housing is greater than on the outside of the inner body.

The configuration of the mixer in which an outlet is formed in the front region of the inner body is expedient, in particular, when rotation of the strand of paste passing out is to be avoided. Moreover, it is possible for an application instrument to be filled directly from the mixer outlet. As the number of outlets increases, it is possible to increase the delivery quantity of mixed substance.

The dimensions of the mixer may be selected in dependence on the purpose for which the latter is to be used and may basically be as desired.

The length and/or the diameter of the mixer usually lie in the range of from 5 to 1000 mm, preferably in the range of from 10 to 100 mm.

The surface area of the inlet openings conventionally lies in the range from 0.1 to 5000 mm$^2$, preferably in the range of from 1 to 400 mm$^2$.

It may also be advantageous if the flow paths which the substances which are to be mixed have to pass on their way from the inlet opening to the outlet have different volumes. This may be achieved by a different path length and/or the installation of a so-called pre-chamber. This ensures that, at the beginning of the mixing operation, one substance always enters into the mixing chamber before the other substance. A specific embodiment and further background details are described, for example, in EP-A-0 993 863.

The apparatus according to the invention in the form of a dynamic mixer usually comprises at least two components which can be separated from one another, the stator and the housing, which may be produced independently of one another.

Suitable materials for the mixer include metals, such as iron, aluminum, titanium, copper, zinc or alloys thereof and/or plastics, such as PE, OPP, PP, PTFE, PC, POM, PA and ABS or mixtures or copolymers thereof. The materials are preferably used in fiber-reinforced and/or filled form.

Suitable fibers and fillers include glass fibers/particles and carbon fibers/particles.

Suitable mixers may be produced, for example, by injection molding, if appropriate by two-component injection molding.

Depending on the substance which is to be mixed, the mixer is preferably designed as a disposable part and is only intended for single use.

The mixer is usually operated at a speed in the range of from $10^1$ to $10^4$, preferably in the range of from $10^2$ to $10^3$, rpm.

The mixers according to the invention can be used in all sectors of technology, in particular for mixing highly viscous, pasty and/or thick-flowing compounds.

These include, in general, substances which are stored separately in at least two components and have to be mixed prior to use.

Examples of these are adhesives, joint-filling compounds and coatings.

The mixers according to the invention may preferably be used in the dental sector. The apparatuses according to the invention are particularly suitable for mixing highly viscous impression materials which, by means of electrically driven pistons, are forced, for example, out of tubular bags which have been pushed into suitable cartridges. It is also conceivable and possible for the materials to be discharged from suitable cartridges which are filled directly with the material without a tubular bag being used.

The term highly viscous compounds covers all compounds with a viscosity determined by the consistency test in accordance with DIN 4823 class 0 to 3, with a diameter of less than 80 mm.

Examples of materials which may be mentioned are silicones, polyethers, epoxides and polyurethanes.

For operating the mixer, use is usually made of a mixing arrangement comprising a delivery unit for the substances which are to be mixed and a drive unit for the dynamic mixer. The drive unit of a suitable mixing arrangement does not open out into the common axis formed by the housing and inner body of the mixer. Possible configurations for suitable drive units are described in conjunction with the figures.

The invention also relates to the use of the mixer and of the above-described mixing arrangement in particular for providing dental materials.

A suitable process here comprises the following steps: a) continuously introducing into the inlet openings of the mixer at least two substances which are to be mixed, b) rotating the housing of the mixer.

The present invention also relates to a kit comprising the dynamic mixer and a cartridge with at least two openings and at least two chambers for accommodating substances which are to be stored separately. The inlet openings of the mixer here can be connected reversibly, or are already connected fixedly, to the outlet openings of the cartridge.

Figure 2:
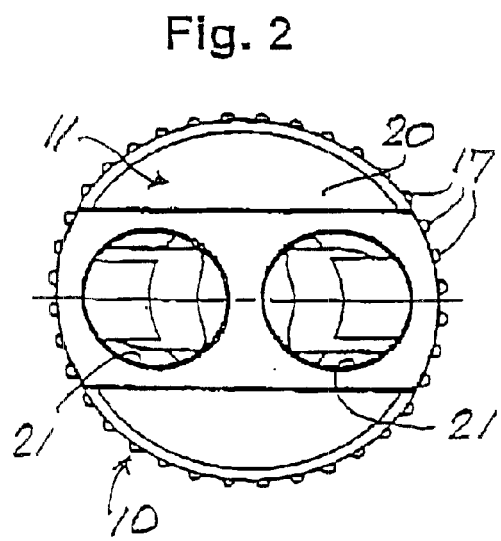
Figure 3:
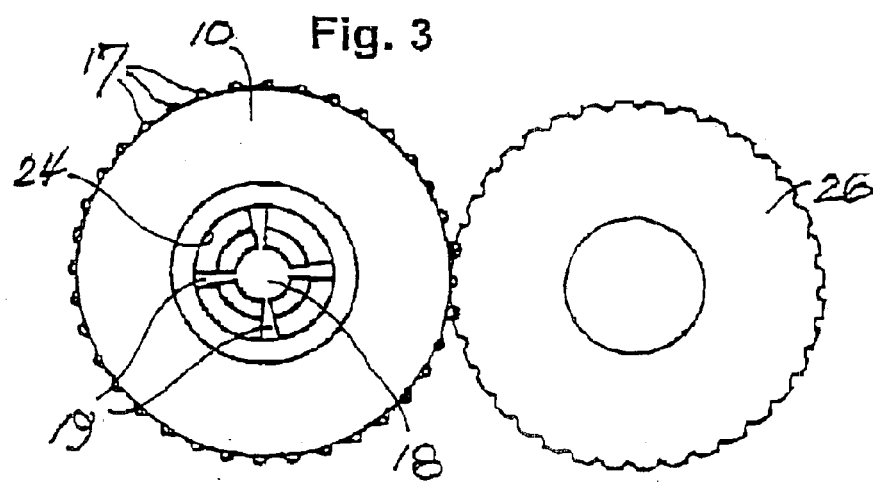
Figure 4:
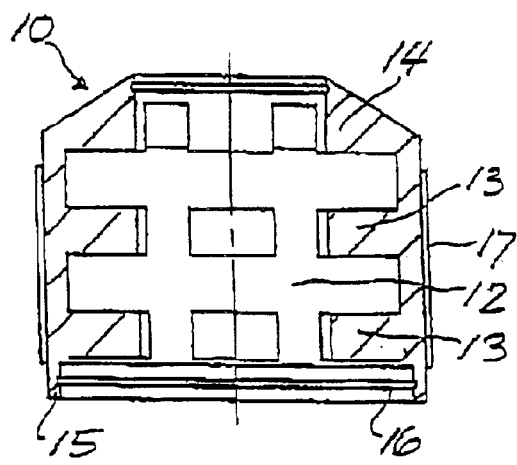
Figure 5:
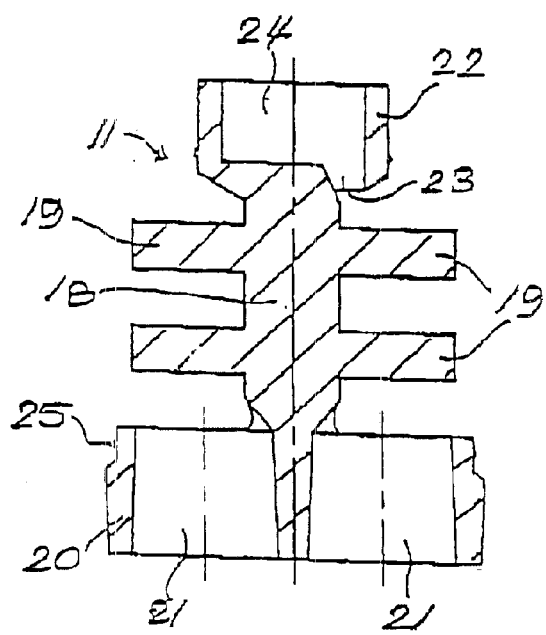
Figure 6:
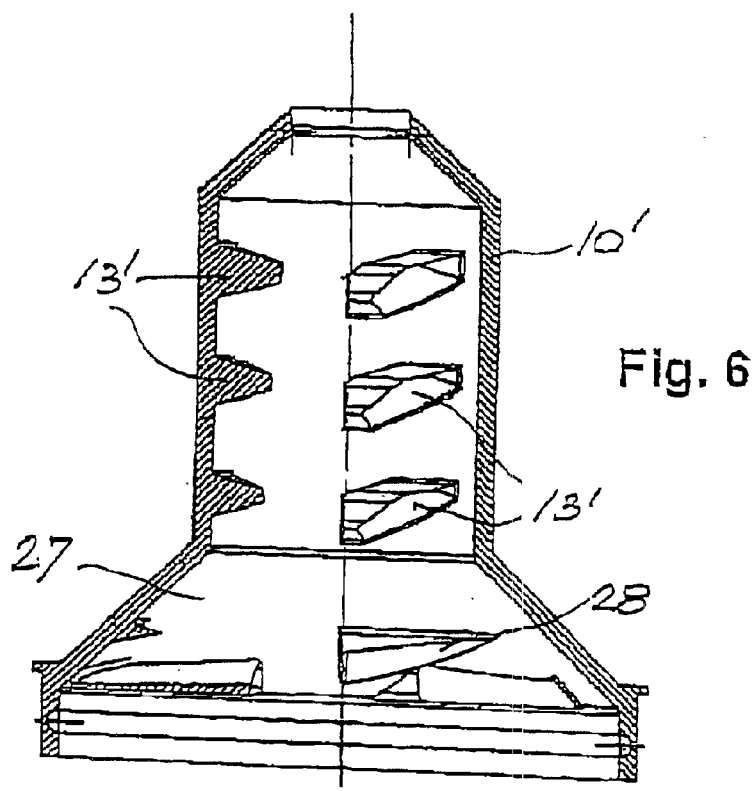

Exemplary embodiments of the invention are explained in more detail hereinbelow with references to the drawings, in which:

FIG. 1 shows a longitudinal section through a dynamic mixer,

FIG. 2 shows an end view of the mixer, as seen in the direction of the arrow II according to FIG. 1, FIG. 3 shows a plan view of the mixer including a drive element, as seen in the direction of the arrow III according to FIG. 1, FIG. 4 shows the housing of the mixer according to FIGS. 1 and 2, FIG. 5 shows the inner body of the mixer according to FIGS. 1 and 2, FIG. 6 shows a longitudinal section through the housing of a mixer according to a further exemplary embodiment, FIG. 7 shows a view, partly in section, of the inner body of the mixer according to FIG. 6, and FIG. 8 shows a plan view of the outlet end of a mixer with a drive element.

The dynamic mixer illustrated in FIGS. 1 to 5 comprises a housing 10, which forms the rotor of the mixer, and an inner body 11, which forms the stator.

According to FIGS. 1 and 4, the housing 10 is a constituent part of an essentially cylindrical mixing chamber 12, from the inner wall of which, as appropriate, mixer blades 13 project radially inward. The mixer blades 13 are arranged in two planes one behind the other in the axial direction of the mixer housing 10, four mixer blades being offset through respectively 90° in each plane.

At the outlet end, the housing 10 has at least one annular inwardly extending portion 14, which serves for mounting on the inner body 11. The opposite end of the housing 10, said end being directed toward the inlet, is provided, for example, with an annular flange 15, which may have an inner annular groove 16 for the axial guidance of the rotating housing.

As can be seen from FIGS. 2 and 3 in particular, the housing 10 is provided, over the entire outer circumference of its cylindrical part, with a drive region 17, for example an arrangement of teeth or grooves.

According to FIGS. 1 and 5, the inner body 11 preferably has a central cylindrical core 18 which is adjoined by mixer blades 19, for example, in two axially offset planes. Four mixer blades 19 offset through respectively 90° are provided, as appropriate, in each plane.

At the inlet end, the core 18 has a termination element 20, through which, for example, two diametrically opposite inlet channels 21 pass. At the outlet end, the core 18 bears a tubular connector 22, of which the connection to the core 18 is interrupted at at least one location in order to form a through-passage opening 23 and which forms, at the other end, an outlet channel 24 of the mixer.

In the plan view of the outlet end of the mixer which is shown in FIG. 3, it is also possible to see the four mixer blades 19 of the stationary core 18.

The inner body 11 shown in FIG. 5 is arranged in the housing 10, which is shown in FIG. 4, such that the mixer blades 19 of the inner body 11 engage in the interspaces between the mixer blades 13, or the mixer blades 13 and the annular inwardly extending portion 14, of the housing 10. At the same time, the annular groove 16 provided, as appropriate, on the bottom annular flange 15 of the housing 10 for latching with an annular bead 25 provided on the rear termination element 20 of the inner body 11. As a result, the inner body 11 and housing 10 are aligned in the axial direction such that the mixer blades 13, 19 can be moved relative to one another with a small spacing between them. It is also possible, however, for such an annular groove not to be provided and for the axial alignment of the inner body to be provided predominantly by the mixer blades, although this may result in relatively high frictional resistance.

Further axial mounting of the housing 10 and inner body 11 is achieved, at the rear end, by the engagement of the termination plate 20 of the inner body 11 in the annular flange 15 of the housing 10 and, at the outlet end, by the engagement of the tubular connector 22 of the inner body 11 in the annular inwardly extending portion 14 of the housing 10.

For fitting in place, for example, a mixing arrangement on a discharging apparatus (not shown), the two inlet channels 21 of the inner body 11 are plugged onto corresponding outlet nipples of the apparatus or of cartridges which are positioned in the apparatus. If the discharging apparatus is started up, then a drive element 26, which is made to rotate by a motor of the apparatus and which is the exemplary embodiment shown in FIG. 3 is a gearwheel, engaged with the arrangement of teeth or grooves 17 on the outside of the housing 10, with the result that the housing 10 is made to rotate about the stationary inner body 11.

In FIG. 3, the drive element 26 comprises a single gearwheel. An advantageous configuration is one in which a plurality of drive gearwheels, distributed over the circumference of the housing 10, engage in the arrangement of teeth or grooves 17 because, at the same time, this avoids the mixer yielding laterally and being loaded on one side.

Instead of the gearwheel shown in FIG. 3, it is also possible for the drive element 26 to be a toothed belt, driven by a motor of the apparatus, or a sleeve (hollow pinion) which encloses the housing 10, as is shown in FIG. 8. In a further variant, it is possible for the outer circumference of the housing 10 to be smooth and to interact with one or more frictional drive wheels or a frictional belt.

In a preferred embodiment, it is also possible for the driving to take place via carry-along pins, which may engage in protrusions on the outside of the housing of the mixer. A number of carry-along pins in the range of from 1 to 5, particularly preferably 2 to 4, in particular 3, is advantageous.

At the same time, pistons provided in the apparatus force the two components into the inlet channels 21. The components, which are mixed intensively with one another by the interengaging mixer blades 13, 19, are forced forward in the mixer by the discharging force created by the pistons, the mixed paste passing, through the through-passage opening 23, into the outlet channel 24 and, from there, being discharged to the outside.

The dynamic mixer according to the above exemplary embodiment serves for producing a paste from two components. In order to produce mixtures from three or more components, the inner body 11 or the termination element 20 has a correspondingly greater number of inlet channels 21, which are preferably, but not necessarily, distributed at equal angles around the axis.

It is likewise the case that the above details in respect to the number of mixer-blade planes, the number of mixer blades 13, 19 in each plane and the distribution of the mixer blades over the circumference are only exemplary embodiments. The numbers and details mentioned can be selected freely in dependence on the properties of the components and of the mixture which is to be produced.

The exemplary embodiment shown in FIGS. 6 and 7 differs from that according to FIGS. 1 to 5, inter alia, in that the inlet channels 21' have different cross sections and are located further away from the common axis of the housing 10' and the inner body 11'. Accordingly, the housing 10' and the inner body 11' have a conically narrowing inlet region 27, in which there are provided correspondingly longer mixer blades 28 (in the housing 10') and 29 (on the inner body 11'). In the cylindrical part of the mixing chamber 12', the housing, furthermore, has three planes each with three mixer blades 13' which are offset at equal angles around the axis and are located in interspaces between the mixer blades 19' of the inner body 11', the mixer blades 19' being arranged in a total of four planes. It is also the case on the inner body 11' that three mixer blades 19' are distributed at equal angles around the axis in each plane.

The dynamic mixer according to FIGS. 6 and 7 has slightly larger spacings between the respective mixer blades 13', 19' than the dynamic mixer according to FIGS. 1 to 5, and is thus suitable for more highly viscous compounds. For sufficiently intensive mixing, the mixer blades 13', 19' here are arranged in a greater number of planes, this resulting in a somewhat increased axial length of the mixer.

List of Designations

10 Housing
11 Inner body
12 Mixing chamber
13 Mixer blade (of the housing 10)
14 Inwardly extending portion
15 Annular flange
16 Annular groove
17 Drive region, for example arrangement of grooves
18 Core
19 Mixer blade (of the inner body 11)
20 Termination element
21 Inlet channels
22 Tubular connector
23 Through-passage opening
24 Outlet channel
25 Annular bead
26 Drive element
27 Inlet region
28 Mixer blade (of the housing 10')
29 Mixer blade (of the inner body 11')

What is claimed is:

1. A dynamic mixer comprising a housing and an inner body, which can be rotated relative to one another about a common axis and, at least in part, form a mixing chamber,
    a termination element, which bounds the mixing chamber and has inlet openings for feeding the components which are to be mixed,
    at least one outlet for discharging the mixture, and
    a drive region which is provided on the rotatable part of the mixer,
    the inner body and the termination element forming the stator of the mixer, and the housing forming the rotor of the mixer.
2. The dynamic mixer as claimed in claim 1, in which the drive region is arranged eccentrically in relation to the axis.
3. The dynamic mixer as claimed in claim 1, in which interengaging mixer blades are provided on the outside of the inner body and on the inside of the housing.
4. The mixer as claimed in claim 1, in which the outlet is provided at an end face of the inner body.

5. The mixer as claimed in claim 1, in which the housing has a drive region on its outer circumference.
6. The mixer as claimed in claim 5, in which the drive region is driven in a non-positively locking manner.
7. The mixer as claimed in claim 5, in which the drive region is driven in a positively locking manner.
8. A kit comprising a dynamic mixer as claimed in claim 1 and a cartridge with at least two openings and at least two chambers for accommodating substances which are to be stored separately, it being the case that the inlet openings of the mixer can be connected reversibly, or are already connected fixedly, to the outlet openings of the cartridge.
9. A mixing arrangement comprising a delivery unit for the substances which are to be mixed, a drive element and a dynamic mixer as claimed in claim 1, the drive element not opening out into the common axis formed by the housing and inner body of the mixer.
10. The mixing arrangement as claimed in claim 9, the drive element being selected from carry—along pins, gearwheels, hollow pinions, frictional wheels, frictional belts and toothed belts.
11. A mixing process comprising the following steps: a) introducing into the inlet openings of a mixed as claimed in claim 1 at least two substances which are to be mixed, b) rotating the housing of the mixer.
12. Use of a mixer as claimed in claim 1 for mixing dental compounds.
13. Use of a kit as claimed in claim 8 for mixing dental compounds.
14. Use of a mixing arrangement as claimed in claim 9 for mixing dental compounds.
15. A dynamic mixer for mixing a plurality of components to form a dental compound mixture comprising:
    an inner body
    a housing surrounding the inner body with formation of a mixing chamber,
    inlet openings to the mixing chamber for accommodating supply of components to be mixed,
    at least one outlet for discharging a mixture formed in the mixing chamber, and
    drive structure provided on the housing for accommodating driving of the housing with respect to the inner body to carry out mixing operations in the mixing chamber.
16. A dynamic mixer according claim 15, wherein said housing and inner body are rotatable with respect to one another about a common axis.
17. A dynamic mixer according to claim 16, wherein said inner body is rotably fixed and said housing is rotated with respect to the inner body during mixing operations, and
    wherein the inlet openings are provided on one axial end of the inner body.
18. A dynamic mixer according to claim 15, wherein interengaging mixer blades are provided on a radial outer surface of the inner body and a radial inner surface of the housing.
19. A dynamic mixer according to claim 17, wherein interengaging mixer blades are provided on a radial outer surface of the inner body and a radial inner surface of the housing.
20. A dynamic mixer according to claim 15, wherein said drive structure includes gear structure engageable with gear structure of a driving gear.
21. A dynamic mixer according to claim 15, wherein said drive structure includes a surface engageable with a drive belt operable to rotate the housing.

22. A method of making a dental compound mixture by mixing a plurality of components to form the dental compound mixture using a dynamic mixer which has an inner body, a housing surrounding the inner body to form a mixing chamber together with the inner body, inlet openings to the mixing chamber for supplying respective components, and at least one mixing chamber outlet opening for discharging a dental compound mixture from the mixing chamber, said method comprising:

supplying components under pressure through the inlet openings to the mixing chamber, and mixing the components in the mixing chamber by rotatably driving the housing around the inner body while maintaining the inner body in a relatively fixed position.

23. A method according to claim 22, wherein said housing and inner body are rotatable with respect to one another about a common axis.

24. A method according to claim 23, wherein interengaging mixer blades are provided on a radial outer surface of the inner body and a radial inner surface of the housing.

25. A method according to claims 24, wherein said inlet openings are provided on an axial end of the inner body, and wherein said supplying components includes placing at least one component containing cartridge in communication with respective ones of said inlet openings and applying pressure to the components in said at least one cartridge.

26. A kit including:

at least one cartridge containing respective viscous components for forming a dental compound, and a dynamic mixer for mixing the components from the at least one cartridge, said dynamic mixer comprising:

an inner body a housing surrounding the inner body with formation of a mixing chamber, inlet openings to the mixing chamber for accommodating supply of components to be mixed, at least one outlet for discharging a mixture formed in the mixing chamber, and drive structure provided on the housing for accommodating driving of the housing with respect to the inner body to carry our mixing operations in the mixing chamber.

27. A kit according to claim 26, wherein said housing and inner body are rotatable with respect to one another about a common axis.

28. A kit according to claim 27, wherein said inner body is rotably fixed and said housing is rotated with respect to the inner body during mixing operations, and wherein the inlet openings are provided on one axial end of the inner body.

29. A kit according to claim 27, wherein interengaging mixer blades are provided on a radial outer surface of the inner body and a radial inner surface of the housing.

30. A cartridge adapted to supply at least one component to a dynamic mixer for mixing a plurality of components to form a dental compound mixture, said dynamic mixer comprising:

an inner body a housing surrounding the inner body with formation of a mixing chamber, inlet openings to the mixing chamber for accommodating supply of components to be mixed, at least one outlet for discharging a mixture formed in the mixing chamber, and drive structure provided on the housing for accommodating driving of the housing with respect to the inner body to carry our mixing operations in the mixing chamber, wherein said cartridge is adapted to interface with at least one of said inlet openings during mixing operations.

31. A cartridge according to claim 30, wherein said inner body includes a pair of inlet openings disposed side by side about an end of said inner body, and wherein said cartridge includes a pair of chambers adapted to interface with the inlet openings.

* * * * *

UNITED STATES PATENT AND TRADEMARK OFFICE
CERTIFICATE OF CORRECTION

PATENT NO. : 6,837,399 B1  
DATED : January 4, 2005  
INVENTOR(S) : Wagner et al.

It is certified that error appears in the above-identified patent and that said Letters Patent is hereby corrected as shown below:

Column 9,
Line 22, delete "claims" and insert -- claim --, therefor.

Column 10,
Lines 3 and 30, delete "our" and insert -- out --, therefor.

Signed and Sealed this

Fourth Day of October, 2005

JON W. DUDAS
*Director of the United States Patent and Trademark Office*